United States Patent [19]

Johnson

[11] 4,442,917

[45] Apr. 17, 1984

[54] VENTED ACOUSTIC EAR MOLD FOR HEARING AIDS

[76] Inventor: Rubein V. Johnson, 2432 Court St., Muskogee, Okla. 74401

[21] Appl. No.: 429,037

[22] Filed: Sep. 30, 1982

Related U.S. Application Data

[62] Division of Ser. No. 226,030, Jan. 19, 1981.

[51] Int. Cl.³ .............................................. A61B 7/02

[52] U.S. Cl. .................................... 181/135; 181/130

[58] Field of Search ........................ 181/130, 134, 135; 179/107 E, 107 R, 182 R, 182 A, 107 FD, 107 BC, 107 H, 107 S; 330/65

[56] References Cited

U.S. PATENT DOCUMENTS

| | | | |
|---|---|---|---|
| 3,702,123 | 11/1972 | Macken et al. | 179/107 E |
| 3,921,756 | 11/1975 | Johnson | 181/135 |
| 4,010,820 | 3/1977 | Johnson | 181/135 |

*Primary Examiner*—Benjamin R. Fuller

*Attorney, Agent, or Firm*—Head, Johnson & Stevenson

[57] ABSTRACT

An acoustic ear mold insertable into the ear of an individual with impaired hearing and used in conjunction with a hearing aid having a central metal tube surrounded by a larger diameter metal tube defining a closed resonance chamber so that sound energy from the hearing aid is conducted to the ear mold through the central tube where it is reinforced by resonance in the annular chamber before passing on to the inner ear of the user.

8 Claims, 7 Drawing Figures

VENTED ACOUSTIC EAR MOLD FOR HEARING AIDS

This is a divisional application of Ser. No. 226,030, filed Jan. 19, 1981.

CROSS-REFERENCE TO RELATED PATENTS

This application is related to U.S. Pat. Nos. 3,921,756 issued Nov. 25, 1975 and 4,010,820, issued Mar. 8, 1977, of the same inventorship as this application. U.S. Pat. Nos. 3,921,756 and 4,010,820 are inserted into this application by reference.

BACKGROUND OF THE INVENTION

1. Field of the Invention

This invention relates to hearing aids and more particularly to an ear mold for a hearing aid which incorporates a plurality of reflection and resonance chambers.

2. Description of the Prior Art

Heretofore, hearing aids have been developed for amplifying sound waves and to conduct the amplified waves to the tympanic membrane of the ear, in order to improve the hearing of an individual. Presently manufactured hearing aid apparatus includes an amplifier, transducer, and an ear mold, all of parts of which are insertable into the ear.

Amplified sound wave energy created by the amplifier and transducer is usually air conducted to the ear mold, wherein the longitudinal canal or conduit conveys the amplified sound wave energy to the tympanic membrane of the ear, where the normal hearing process is commenced. That is, the sound energy strikes the tympanic membrane and then travels onto the malleus, the incus, the stapes, to the oval window, and on through the fluid of the inner ear, where the cochlea contains the Organ of Corti with associated nerve endings of the auditory nerve from the brain.

A disadvantage of the presently manufactured ear molds is that improved hearing is contingent solely upon sound wave amplification. If, for example, otosclerosis has rendered immovable, or partially immovable, the stapes due to ankylosis in the oval window, the effectiveness of a hearing aid is lost. Also, in many instances where a high level amplification is necessary, sound saturation results, whereby the normal process is not aided insofar as intelligibility is concerned.

In addition to the normal air conduction process of hearing by way of the tympanic membrane, sound wave energy can also be conducted to the hearing part of the brain by means of bone conduction. In bone conduction hearing, vibratory sound wave energy is transmitted to the brain over a separate and distinct route from the normal hearing process. Sound wave energy directly enters the mastoid process and other associated bones of the head and travels by bone conduction to the hearing part of the brain for discrimination and interpretation. Thus bone conduction hearing can be beneficial in reinforcing sound wave energy transmitted to the brain by the normal air conduction process.

OBJECTS OF THE INVENTION

It is therefore an object of this invention to provide an improved acoustic ear mold for bone conduction of sound wave energy in combination with conventional airborne sound wave energy to the ear.

It is another object of this invention to provide an improved ear mold wherein amplified sound waves are conducted to the tympanic membrane of the ear and simultaneously therewith to the bones of the mastoid process, and other bones, such that sound wave energy is conveyed by two separate routes to the hearing, understanding part of the brain, for speech and sound discrimination, interpretation and understanding.

It is a further object to provide an improved ear mold having means by which more parameters of the processing of the sound going into the ear of the user from the hearing aid, can be varied, to properly match the process of the sound by the ear mold to the acoustic properties of the hearing system of the user.

It is a still further object of this invention to provide an ear mold for a hearing aid in which a plurality of resonance chambers are provided inside of the ear mold for the purpose of filtering and amplifying selected frequencies in the acoustical wave being propagated into the ear through the ear mold and to provide at least two paths for the transmission of acoustic energy from the ear mold to the brain of the user, one of these through the airborne acoustic energy transmitted through the central tube of the ear mold to the tympanic membrane, and the other through the vibrating surface of the outer metal shell surrounding the resonance chamber, the wall of the outer shell being in close proximity to the wall of the ear canal of the user, and therefore in close proximity to the mastoid structure of the ear.

SUMMARY OF THE INVENTION

These and other objects are realized and the limitations of the prior art are overcome in this invention by providing at least one resonance chamber which surrounds the tubular channel for acoustical energy transmission from the hearing aid amplifier and transducer, through the ear mold and into the ear.

The resonance chamber in the first type is an annular space between the central tube and a larger diameter tube, which is closed by annular end plates, to which the two tubes are sealed. There is an opening in the wall of the central tube which connects the annular resonance chamber with the inner passage or conduit of the ear mold.

In the second type the resonance chamber consists of the central tube as above, but the outer wall of the chamber is not tubular but conforms to the shape of the auditory canal of the user. At the rear it is enclosed by a more or less annular end plate. A small diameter metal tube may be inserted through the metal shell and the end plate connecting with a hole through the plastic base of the ear mold venting the space inside the auditory canal to the atmosphere.

In the third type the cylindrical resonance chamber of the first type is used to generate the resonance which is conducted to the open-ended shell of the second type which is in contact with the bones and tissue of the external auditory canal, the hole opened up as much as possible to give maximum venting to the atmosphere, yet provide maximum resonance for bone conduction.

The central tube in all cases has two internal diameters achieved by machining or swaging the small diameter toward the ear drum giving a compression to intensify the sound wave as it enters the chamber. The opening through the wall of the central inner tube in its larger diameter may be a single circular opening, or it may be a complete opening or gap around the wall, except for one or more narrow wires or posts joining the two parts of that inner tube.

In the plastic molded portion of the ear mold, the central passage or conduit that joins the inner end of the central tube, may be increased in diameter to a selected diameter over a selected length, to form a small cylindrical resonance chamber, with its size determined by the size of the individual ear mold.

BRIEF DESCRIPTION OF THE DRAWINGS

These and other objects of this invention and a clear understanding of the principles and details of the invention will be evident from the following description taken in conjunction with the appended drawings in which.

DESCRIPTION OF THE PREFERRED EMBODIMENT

Figure 1:
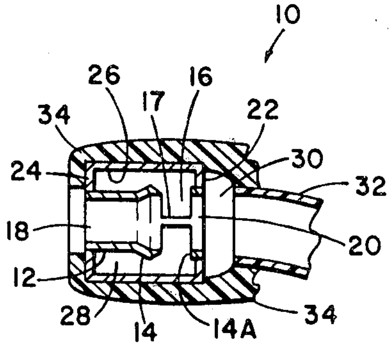
FIG. 1 is a cross-sectional view of a first embodiment of this invention.
Figure 6:
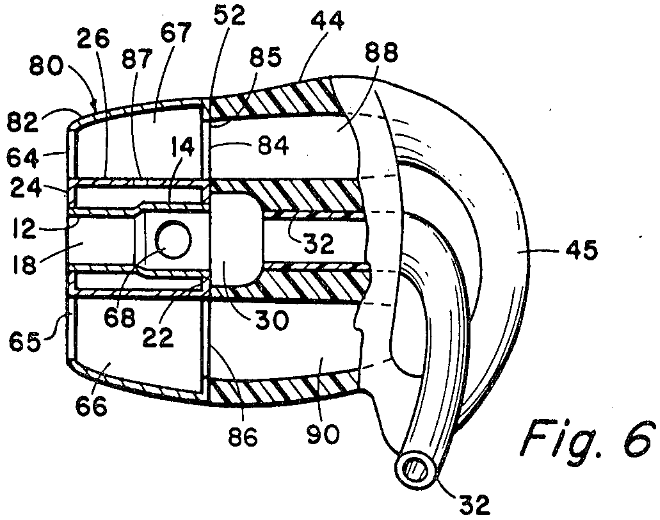
FIG. 6 shows the same device as in FIG. 5 but the view is rotated 90 degrees.

Referring now to the drawings and in particular to FIG. 1, there is shown an ear mold identified generally by the numeral 10, which is somewhat similar to the embodiment of FIG. 6 of my U.S. Pat. No. 4,010,820, which has been entered by reference into this application. However, there are a number of improvements in FIG. 1 over that of FIG. 6 of the '820 patent, which will be evident as the description proceeds.

There is an inner central tube 12 which has a larger diameter portion designated as 14 and 14A. There may be one or more thin, wire-like support posts 17 between the portions 14 and 14A, which holds them in coaxial alignment leaving a gap 16 between the two parts. The gap 16 may be of any selected length corresponding to the lengths of the posts 17. Posts 17 serve to hold portions 14 and 14A in alignment during fabrication of the ear mold. With different manufacturing techniques the posts 17 may be eliminated; and when posts 17 are not used, better high frequency response is achieved.

There is an outer cylindrical thin metal wall 26, which is coaxial with the central tube 12, 14, the diameter of the outer wall being larger than that of the tube 12 by a selected amount and the annular space 28 between the two tubular portions is closed off by means of annular end walls 22 on the outer end, and 24 on the inner end. Thus, the annular space 28 forms a resonating chamber, the frequency of resonance of which is determined by the volume of the annular space 28, and the dimensions of the gap 16 between the two portions 14 and 14A. Thus, adjustment of this dimension 16 can be made to alter the frequency of resonance of this annular chamber 28.

On the outer end of the assembly 10 is a cavity 30 formed on the interior of the plastic covering 34, providing a cavity volume 30. A thin-walled plastic tube 32 is inserted into an opening in the inner end of the ear mold leading into the first cavity 30 and then into the inner tube 14A, 14, 12. There are, therefore, two resonant chambers, the chamber 30 and the resonating space 28.

Figure 2:
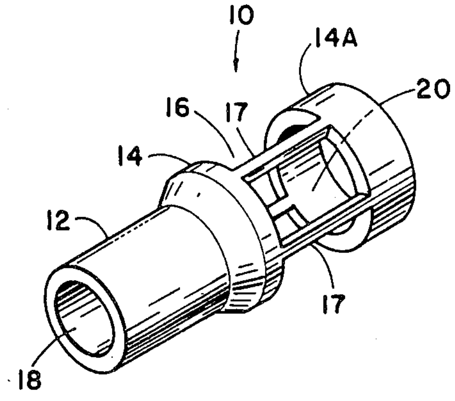
FIG. 2 illustrates the metallic inner portion of the apparatus of FIG. 1 to an enlarged scale.

Referring now to FIG. 2, there is shown to enlarged scale a part 12, 14, 14A of the metal portion 10 of the ear mold of FIG. 1. This shows clearly the step between the two diameters of the portions 12 and 14. The reduced diameter 12 is necessary to give a compression to the sound wave as it enters the resonance chamber. The inner tube 12, 14, 14A is connected at its outer end 14A to the cavity 30, and at its inner end to the space inside of the auditory canal near to the tympanic membrane. As previously mentioned, the longitudinal spacing between the portions 14 and 14A can be made of any selected length. The two portions are held together by one or more narrow posts 17, so as to maintain the two portions 14, 14A in fixed coaxial alignment and constant gap dimension.

Figure 3:
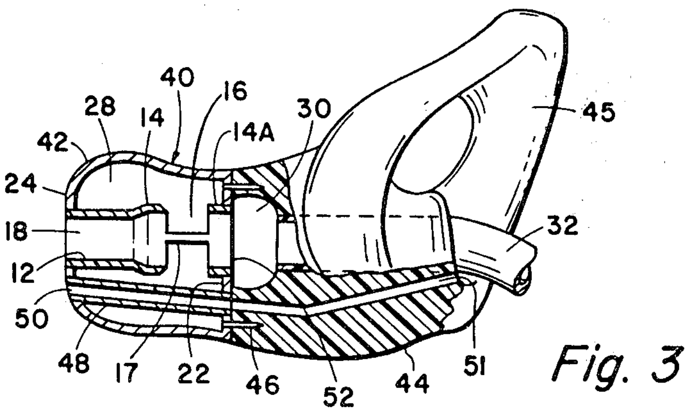
FIG. 3 is an external view, shown partially in cross-section, illustrating a second embodiment based upon the embodiment of FIG. 1.

Referring now to FIG. 3, there is shown a second embodiment 40 of the apparatus of FIGS. 1 and 2. Here again is shown the inner tube 12, 14, 14A of FIG. 2 with the central opening 18. The outer wall 42 surrounding the inner tubular portion 12 is made of thin-walled metal of selected character (such as gold, for example) in the shape of an auditory canal of the user. Thus, it presses against the wall of the auditory canal at positions which are in close proximity to the mastoid bone of the user.

This construction differs appreciably from that of FIG. 1 in that the outer wall of the resonance chamber 28 is now in direct contact with the wall of the auditory canal which is in close proximity to the mastoid bone, where as in FIG. 1 the outer wall 26 was spaced away from the auditory wall of the auditory canal by a molded plastic portion 34.

The resonance chamber 28 again serves the same purpose as the chamber 28 in FIG. 1, but because of the shape of the outer wall 42 and of its thinness, it will vibrate in resonance with the air in the space 28, and thus will conduct the vibrations of the air space to the bones and tissue of the external auditory canal. Thus, the auditory signals are carried to the brain by air and bone conduction.

There is one further modification of FIG. 3 over FIG. 1; that is, the presence of a vent tube 48 of metal, having an inner opening 50. The metal tube is sealed into the inner and outer walls of the resonance chamber 28 and connects with a tubular opening 51 through the ear mold, out to the atmosphere. This provides a means for controlling the sound pressure inside of the ear to a value which may be different for each user. Venting ear molds to permit pressure equalization in a known technique.

Figure 4:
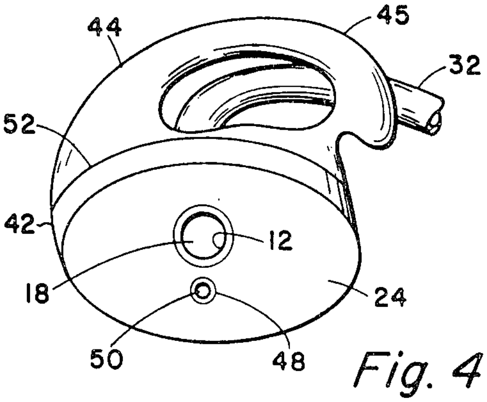
FIG. 4 is an end view of the embodiment of FIG. 3.

FIG. 4 shows the inner end of the ear mold of FIG. 3. It shows the opening 18 formed by the inner tubular member 12 and the opening 50 of the vent tube 48. The line 52 shows the joining plane between the metal surface 42 of the ear mold to the plastic portion 44.

Figure 5:
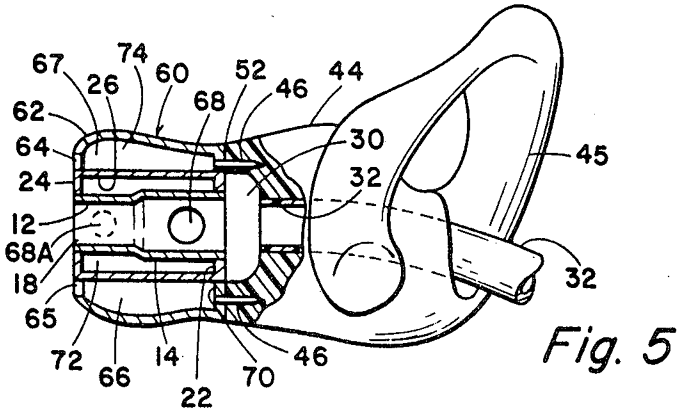
FIG. 5 is an external view, shown partially in cross-section, of a third embodiment of this invention.
Figure 7:
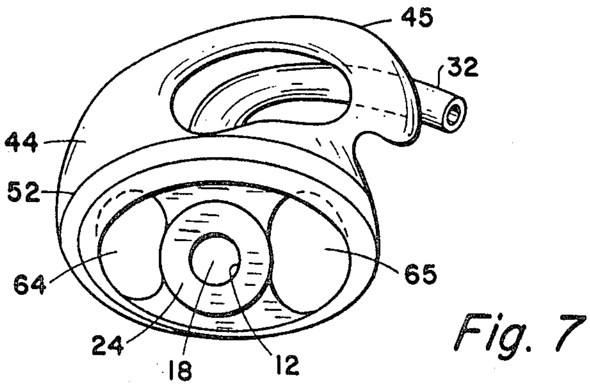
FIG. 7 is an end view of the embodiments of FIGS. 5 and 6.

Referring now to FIGS. 5, 6, and 7, there is shown another embodiment of this invention in which the resonance chamber of FIG. 1 is incorporated in a truncated section of the outer shell of FIG. 3. The inner end portion (that surface nearest the ear drum) of FIG. 3, number 42, is cut off and becomes number 60 of FIG. 5. The purpose of this design is to leave as large an opening as possible yet give a resonating surface in contact with the wall of the auditory canal. The thin-walled metal shell 60 is in contact with resonating chamber 26 by having been soldered at assembly to projecting sections of rear wall 85 through which holes 84 and 86 vent the sound pressure generated in cavity 66 and 67 (or 74) to the atmosphere.

In the inner tube section 14 of FIG. 5 the orifice may be as shown in 68, or it may be a gap as shown in FIG. 3, number 16.

Referring to FIG. 5, the openings 64 and 65 in the thin-walled shell 62 should be as large as possible, cutting out the whole end of the shell, leaving only a rounded radius to eliminate any sharp edges in contact with the tissue of the auditory canal.

FIG. 6 is the same item as FIG. 5 except that the view has been rotated 90 degrees. In place of the section having been cut through the pins, it has been cut through the holes, and those holes are as large as possible.

In FIGS. 5 and 6 the opening 68 can be in either the large diameter portion 14 of the inner thin-walled metal tube, or in the smaller diameter portion 12, shown as dashed circle 68A. Numeral 72 represents the volume of the first resonance chamber. In FIG. 6 numeral 80 represents the entire ear mold, while 82 represents the thin outer metal wall of the outer resonance chamber, and both 26 (and 87) represent the outer thin-walled metal tube of the first resonance chamber.

FIG. 7 is an end view of FIG. 6. Holes 64 and 65 vent to the atmosphere through the openings 88 and 90 in the base of the plastic ear mold.

As illustrated in FIG. 3, the metal portion of the ear mold 60 is attached to the plastic portion 44 along the plane 52, and is held in position by means of pins 46 securely fastened to the metal portion 60 and solidly bonded to the plastic portion 44. Here again is shown an additional possible resonance chamber 30 molded into the plastic at the outer end of the metal portion 60, as was shown in FIGS. 1 and 3. Of course, this chamber 30 would not be provided unless needed. If not required, the spaced 30 will then have the same diameter as the opening through the molded portion into which the tube 32 is inserted.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. In a hearing aid ear mold insertable into the auditory canal of the user and having a longitudinal conduit for the passage of sound wave energy from a hearing aid to the tympanic membrane of the ear, the improvement comprising a metal structure having:

(a) an inner central thin-walled metal tube forming said longitudinal conduit, connected at its outer end by tubular means to said hearing aid, the inner end inserted into the ear;

(b) an outer thin-walled metal tube coaxial with said inner central tube, and forming a first annular space closed by annular end walls sealing the annular space between said inner and said outer thin-walled metal tube;

(c) said inner metal tube constructed by cutting a groove of selected width through the wall of said inner tube near one end forming two portions, a long portion on the inner end, toward said tympanic membrane, and a short portion on the outer end; and including at least one slender post holding said two portions in fixed coaxial and spaced relation, whereby the opening between the space in said conduit and in said first annular space is a narrow circumferential gap forming a first resonance chamber.

2. The ear mold as in claim 1 in which said central tube is constructed of two parts of different diameter.

3. The ear mold as in claim 2 in which the portion of largest diameter is connected to the hearing aid tubular member.

4. The ear mold as in claim 3 in which said gap is in the portion of larger diameter.

5. The ear mold as in claim 1 and including a plastic molded member affixed to one end of said metal structure and contoured to fit the ear of the user, and having a passageway therein communicating with said conduit and receiving said tubular means.

6. The ear mold as in claim 5 in which said passageway is enlarged in the vicinity of the outer end of said metal structure to a larger diameter; thus forming an open second resonance chamber of selected diameter and length.

7. The ear mold as in claim 1 including a molded plastic covering over the outer metal tube and inner end of said first resonance chamber, the outer surface of said covering shaped to fit the diameter and surface of the inner wall of said auditory canal.

8. The ear mold as in claim 5 and including a small diameter metal tube passing through said first resonance chamber between the inner wall and outer wall, connecting to a colinear passageway through said molded portion to the atmosphere; resulting in a semi-non-occluded ear mold.

* * * * *